(12) United States Patent
Newman

(10) Patent No.: US 6,321,596 B1
(45) Date of Patent: Nov. 27, 2001

(54) SYSTEM AND METHOD FOR MEASURING AND CONTROLLING ROTATION OF COILED TUBING

(75) Inventor: Kenneth R. Newman, Conroe, TX (US)

(73) Assignee: CTES L.C., Conroe, TX (US)

( * ) Notice: Subject to any disclaimer, the term of this patent is extended or adjusted under 35 U.S.C. 154(b) by 0 days.

(21) Appl. No.: 09/296,024

(22) Filed: Apr. 21, 1999

(51) Int. Cl.$^7$ ............................. E21B 45/00; G01N 3/32

(52) U.S. Cl. ........................................... 73/152.45; 73/811

(58) Field of Search .......................... 73/564.08, 152.04, 73/152.17, 152.44, 152.45, 152.46, 152.52, 808, 811

(56) References Cited

U.S. PATENT DOCUMENTS

| | | | |
|---|---|---|---|
| 2,008,612 | * | 7/1935 | Heath . |
| 2,630,180 | * | 3/1953 | Summers . |
| 2,677,427 | * | 5/1954 | McKinney et al. . |
| 2,720,266 | * | 10/1955 | Broussard et al. . |
| 2,816,439 | * | 10/1957 | McCullough et al. . |

(List continued on next page.)

OTHER PUBLICATIONS

Coiled Tubing Services, Nowsco, Prior to 1998.
"The Coiled Tubing Boom," Petroleum Engineer, Apr. 1991, pp. 16–18, 20.
"Get Downhole Coiled Tubing Data When You Need It, As It Happens." Dowell Schlumberger, 1993.
"Sandrik Seamless Coiled Tubing," Sandvik Steel, 1993.
"CTES, L.C.," CTES, L.C., 1997.
"Coiled–Tubing–Life Modeling," Newman et al, SPE 22820, 1991.
"Installation of 2⅞ in. Coiled Tubing Tailpipes in Line Gas Wells," JPT, May 1994, pp. 442–447.
"Advances Culminate In Smart System," Turner et al, American Oil & Gas Reporter, Apr. 1999, pp. 65–66, 68, 69.
Development And Use of An Analytical Model To Predict Coiled Tubing Diameter Growth, Brown et al, Society of Petroleum Engineers, SPE 38409, 1997.
Defining Coiled Tubing Limits—A New Approach, Newman et al, OTC 8221, 1996.
Coiled–Tubing Stretch And Stuck–Point Calculations, Newman, Society of Petroleum Engineers, SPE 54458, 1999.
The Benefits of Real–Time Coiled Tubing Diameter Measurements, Quigley et al, Society of Petroleum Engineers, SPE 46040, 1998.
Elongation of Coiled Tubing During Its Life, Newman et al, Society of Petroleum Engineers, SPE 38408, 1997.
Use of Fatigue Test Machine to Investigate Coiled Tubing Diameter Growth, Brown, Schlumberger Dowell, 1994.

(List continued on next page.)

*Primary Examiner*—Max Noori
*Assistant Examiner*—Maurice Stevens
(74) *Attorney, Agent, or Firm*—Guy McClung

(57) ABSTRACT

The present invention, in certain embodiments, discloses an apparatus for determining characteristics of coiled tubing that is run in and out of a bore, e.g. a wellbore, for calculating fatigue life of the coiled tubing, the apparatus having a reel structure for said coiled tubing including a reel on which said coiled tubing is wound and a frame supporting the reel for rotation, an injector structure for running the coiled tubing from the reel structure into said bore and for withdrawing said coiled tubing from the bore, sensor apparatus for continuously monitoring sensing and recording rotation of said coiled tubing and for measuring amount of said rotation, said sensor apparatus including apparatus for receiving and transmitting data relating to said characteristics of the coiled tubing, and a computer apparatus for receiving data from said sensor apparatus and processing said data to determine fatigue life of said coiled tubing.

5 Claims, 2 Drawing Sheets

U.S. PATENT DOCUMENTS

| | | | | |
|---|---|---|---|---|
| 3,182,877 | * | 5/1965 | Slator et al. | 166/77 |
| 3,658,270 | | 4/1972 | Slator et al. | 242/54 |
| 3,866,679 | * | 2/1975 | Laky | 166/77 |
| 3,920,076 | * | 11/1975 | Laky | 166/315 |
| 4,071,086 | * | 1/1978 | Bennett | 166/177 |
| 4,091,867 | | 5/1978 | Shannon, Jr. et al. | 166/77 |
| 4,265,304 | | 5/1981 | Baugh | 156/77 |
| 4,456,225 | | 6/1984 | Lucas | 254/134.3 FT |
| 4,515,211 | | 5/1985 | Reed et al. | 166/77 |
| 4,529,148 | | 7/1985 | Hesprich et al. | 242/159 |
| 4,585,061 | | 4/1986 | Lyons, Jr. et al. | 166/77 |
| 4,655,291 | | 4/1987 | Cox | 166/385 |
| 4,850,569 | | 7/1989 | Griffioen et al. | 254/134.4 |
| 4,928,758 | * | 5/1990 | Siegfried, II | 73/155 |
| 5,011,333 | | 4/1991 | Lanan | 405/166 |
| 5,184,682 | | 2/1993 | Delacour et al. | 166/385 |
| 5,188,173 | | 2/1993 | Richardson et al. | 166/77 |
| 5,211,377 | | 5/1993 | Griffioen et al. | 254/134.4 |
| 5,311,952 | | 5/1994 | Eddison et al. | 175/61 |
| 5,324,006 | | 6/1994 | Pickrell | 254/134.3 FT |
| 5,411,085 | | 5/1995 | Moore et al. | 166/242 |
| 5,503,370 | | 4/1996 | Newman et al. | 254/134.3 |
| 5,553,668 | | 9/1996 | Council et al. | 166/77.3 |
| 5,575,332 | | 11/1996 | Wasterval, Jr. | 166/77.1 |
| 5,599,004 | | 2/1997 | Newman et al. | 254/134.4 FT |
| 5,738,173 | | 4/1998 | Burge et al. | 166/385 |
| 5,806,612 | | 9/1998 | Vorhoff et al. | 175/40 |
| 5,813,480 | | 9/1998 | Zaleski, Jr. et al. | 175/40 |
| 5,823,267 | | 10/1998 | Burge et al. | 166/385 |
| 5,826,654 | * | 10/1998 | Adnan et al. | 73/152.52 |
| 5,833,004 | | 11/1998 | Coronado | 166/382 |
| 5,839,514 | | 11/1998 | Gipson | 166/384 |
| 5,842,530 | | 12/1998 | Smith et al. | 175/162 |
| 5,845,708 | | 12/1998 | Burge et al. | 166/77.3 |
| 5,845,711 | | 12/1998 | Connell et al. | 166/384 |
| 5,848,642 | | 12/1998 | Sola | 166/77.2 |

OTHER PUBLICATIONS

The Fatigue Life Of Coiled Tubing, Sisak et al, IADC/SPE 27437, 1994.

Development Of A Standard Coiled–Tubing Fatigue Test, Newman et al, Society of Petroleum Engineers, SPE 26539, 1993.

* cited by examiner

SYSTEM AND METHOD FOR MEASURING AND CONTROLLING ROTATION OF COILED TUBING

BACKGROUND OF THE INVENTION

1. Field Of The Invention
2. Description of Related Art

Coiled tubing is pipe which can be run in and out of a bore, pipeline, tubular string, borehole, or wellbore. In certain embodiments, the coiled tubing is made of plastic, composites, titanium or steel. The tubing is stored on a reel and in winding onto the reel it is bent. Typically the coiled tubing is fed from the reel over a gooseneck of an injector for directing the tubing into a bore hole. The injection operation often results in further bending of the coiled tubing. Often there is some internal pressure inside the coiled tubing while it is being bent. Also axial loads are applied to the coiled tubing both while it is being bent and while it is straight. Repeated bending cycles can damage the coiled tubing. The internal pressure and axial loads can exacerbate this damage. This damage, known as fatigue damage, accumulates until the coiled tubing eventually fails. Failure is defined as the point at which the coiled tubing can no longer hold internal pressure, or, in extreme situations, the point at which the coiled tubing breaks. After use of the tubing downhole, the tubing is withdrawn from the well and rewound on the reel. The reel has a reel support frame normally mounted on a skid. The skid with the reel and wound tubing thereon may be transported from one site to another. Characteristics of the coiled tubing on which accurate data is required involves fatigue and deformation of the coiled tubing. Coiled tubing is fatigued and/or deformed when it is run in and out of a hole or bore particularly from bending and straightening at the reel and/or gooseneck. Fatigue and deformation are dependent also on other various factors such as axial forces applied to the tubing, the fluid pressure within the tubing while it is being bent or straightened, the tubing material, and the internal and external diameters of the tubing. Parameters have been established for selected features or characteristics of the coiled tubing and its usage. The life expectancy of the tubing may be estimated from such parameters. "Fatigue life" is defined as the useful life of the coiled tubing up to the point of failure due to fatigue. In some coiled tubing operations the length of the fatigue life strongly affects the economics of the operation. The coiled tubing is expensive, and must be replaced at the end of its fatigue life or when it has become too deformed to be used.

In certain prior art systems an operator at each job site is responsible for obtaining and recording pertinent data in a database for the coiled tubing. The updating of the database for each coiled tubing reel may be mandated by certain operators and has generally been performed either manually or by a suitable electronic data acquisition system, for example.

Fatigue factors for coiled tubing include the radii of bending, diameter, wall thickness and length of the coiled tubing. Repeated bending cycles, internal pressure and axial loads can cause the coiled tubing to change in diameter, length and wall thickness. Such changes are permanent deformations that can cause problems when using the coiled tubing.

Fatigue tracking systems have been developed to track the bending events and internal pressure along the length of a coiled tubing string. These systems may also track the axial forces applied to the coiled tubing both while bending and while straight. These systems then use mathematical models to predict the fatigue damage and amount of the fatigue life used. Some of these systems also predict the permanent deformation which will occur along the length of the coiled tubing string.

Often the coiled tubing rotates during its use. A certain segment of the coiled leaves the reel in one rotational orientation, and returns in a different rotational orientation. If the segment has rotated, the neutral axis of bending has also changed, changing the fatigue damage and deformation when compared to a segment which has not rotated. Prior art fatigue tracking systems do not take this rotation into account when calculating fatigue damage and deformation. Many current fatigue tracking systems were developed based upon the assumption that the coiled tubing does not rotate. In some tests done to develop such systems, the coiled tubing was not rotated. Thus, in such tests, the impact of rotation on fatigue life and deformation was not measured.

Recent testing performed by the present inventor and his associates included rotation and axial loading along with the bending and internal pressure. This testing revealed that in many cases rotation increases the fatigue life. In some cases rotation also increased the amount of deformation.

When the coiled tubing is being used, rotation is random and uncontrolled. This random rotation may increase the fatigue life. With the current systems which do not take rotation into account, coiled tubing may be scrapped earlier than necessary, sometimes at a large cost to the industry. The present inventor has recognized that monitoring rotation and including it in a fatigue tracking system would allow the life of coiled tubing to be extended in some cases. In other cases controlling rotation of coiled tubing could extend its useful life, and hopefully, optimize it.

There has long been a need, recognized by the present inventor, for a method that takes coiled tubing rotation into account in making fatigue life determinations and for systems useful in such a method.

FIG. 1 shows a prior art coiled tubing system which does not measure the rotation of the coiled tubing. The system is disclosed in U.S. Pat. No. 5,826,654 which is incorporated herein fully by reference. The system of FIG. 1 is a system for sensing, recording, and storing data concerning characteristics of coiled tubing so that the data may be easily retrieved at another job site. A coiled tubing reel is shown at 10 mounted on a skid 12 for transport from one job site to another job site. A reel frame 13 on skid 12 mounts reel 10 for rotation. Coiled tubing shown at 14 is wound onto reel 10 and is unreeled for being injected downhole. Coiled tubing 14 is used for many downhole applications. A gooseneck 18 of a wellhead injection device 16 diverts the coiled tubing 14 vertically downwardly. Wellhead injection device (injector) 16 includes a drive mechanism for forcing tubing 14 downwardly. A lower wellhead structure 20 receives tubing 14 and normally includes a blowout preventor (BOP) stack.

A skid 12 with reel frame 13 and reel 10 thereon may be transported from one job site to another job site often thousands of miles apart. A reel database 22 is permanently mounted on frame 13 for coiled tubing 10 prior to its use at the first job site. The reel database 22 is permanently fixed with and travels with reel 10 for the entire life of coiled tubing 10. Database 22 includes a memory unit where information concerning coiled tubing 12 is stored for retrieval at each job site.

A continuous cable loop 26 originates at a Coiled Tubing Sensor Interface (CTSI) 28 which forms a main data processing unit at a job site and is looped about and between the equipment or various elements of the system for termination back at CTSI 28. Wires in the cable provide power and distribute data to and from various Sensor Interface Modules (SIMS) 30A, 30B, 30C, 30D, 30E, 30F and 30G located along the continuous cable loop 26. The Coiled Tubing Sensor Interface (CTSI) 28 permits an automatic update and maintenance of reel database 22. A Sensor Interface Module (SIM) is provided for monitoring each of the selected characteristics or features of the coiled tubing. The SIMs are capable of receiving and/or sending data concerning the selected characteristics or features. A SIM 30A for reel 10 includes database 22. The location and number of the sensor interface modules (SIMS) might vary from one job site to another job site.

SUMMARY OF THE PRESENT INVENTION

The present invention, in certain aspects, provides a coiled tubing measuring system for measuring rotational orientation of coiled tubing. Such a system can take discrete rotational measurements at one or at a plurality of locations on a length of coiled tubing while it is being unspooled and run into a bore hole and then when it is retrieved from the bore hole and wound back on a reel. Suitable recording, storage, display, transmission and output devices of such a system can also measure, record, display, and transmit parameters that have been measured by the various prior art systems. Computer models according to the present invention use these parameters, including rotation, to calculate the fatigue damage and predict the fatigue life, either in real time while the coiled tubing is being used or after each usage is completed. According to the present invention prior art publicly available models can be modified to account for rotation of tubing, e.g. Cerberus model of CTES, L.C., co-owned with the present invention; CoilCADE model of Schlumberger Dowell; Cycle model of BJ Services; TAS model from Medco company; and CT Life model of Maurer Engineering.

According to the present invention, coiled tubing can be marked and locations of markings can be measured in a variety of ways. In one aspect a visible line is marked along the coiled tubing or a series of visible lines or dots is used along its length. The rotational orientation of the line, lines, or dots is monitored visually, with optical scanning device (s), or with camera(s) and the location from which amount of rotation can be calculated is logged manually or electronically.

In other embodiments a magnetic line or marking is made along the length of the coiled tubing. In other embodiments, groove(s) or mechanical marks are made along the length of the coiled tubing. In each case the appropriate scanning device(s) are used to monitor the rotational orientation of these markings and the rotation is logged.

Coiled tubing may have a longitudinal seam. In one system according to the present invention a scanning device senses this seam and its rotational orientation along the length of the coiled tubing. Such scanning devices may employ a variety of types of sensors known to one skilled in the art of pipe inspection such as ultrasonic sensors, eddy current sensors, gamma ray sensors Hall effect sensors, and x-ray scanners. In one aspect an array of such sensors encompassing the coiled tubing are used. Rotational orientation is determined based upon which sensor(s) in the array sense the seam (or markings) or are closest to it. In another aspect one or more such sensors are rotated around the coiled tubing to find the seam (or markings).

Other systems according to the present invention control the rotation of coiled tubing to increase its useful life. Such systems include an apparatus for gripping the coiled tubing and, when desired, applying rotational torque to control the amount of rotation along the length of the coiled tubing. The amount of rotation applied is determined using the computer models to optimize the fatigue life or to reduce the deformation. In another aspect an injector is modified to apply rotational torque in addition to axial force. In another embodiment a plurality of axially rolling wheels grip the coiled tubing. Powered rotation of these wheels about the coiled tubing axis applies rotational torque to the coiled tubing to control the amount of rotation.

In certain embodiments of the present invention a fatigue tracking system includes these components: electronic data acquisition system, computer with modeling software, sensor(s) and, optionally, a device for applying rotational torque to the coiled tubing. The sensor(s) measure rotational orientation of the coiled tubing in any combination with one, some or all of the following: its depth (length), weight (axial load while straight), internal pressure, reel back tension (axial load while bending), wall thickness diameter and ovality of the coiled tubing. The sensor(s) provide a signal indicative thereof to the data acquisition system which stores this data in a database. The computer system then uses this data to calculate the amount of fatigue damage and deformation for various segments along the length of the coiled tubing. These calculations may be verified with physical wall thickness diameter and ovality measurements. The rotational torque device may be used to control the rotation of the coiled tubing, to optimize the fatigue life and/or to minimize deformation.

Current prior art models, and/or computer programs using them, calculate the strain (stretch) due to bending and the associated fatigue life at one or two points around a coiled tubing cross-section. This point(s) will be the point(s) of maximum strain at the top of the CT cross-section and/or at the bottom of the CT cross-section. Since rotation of the CT is not considered, the strain and fatigue life is not calculated at any other points around the CT cross-section. In one aspect, such models and/or computer calculation programs using them, according to at least certain preferred embodiments of the present invention, do include calculating the strain (stretch due to bending) and the fatigue life caused by this strain at an array or a plurality of points around a particular coiled tubing cross-section, since strain and fatigue life at different points of such a cross-section differ with differing rotational orientations. In certain preferred embodiments, such calculations are made for 4, 8, 16 or more points around a coiled tubing cross-section. In other embodiments these calculation points may be spread around only a portion, e.g. half, of the coiled tubing cross-section.

What follows are some of, but not all, the objects of this invention. In addition to the specific objects stated below for at least certain preferred embodiments of the invention, other objects and purposes will be readily apparent to one of skill in this art who has the benefit of this invention's teachings and disclosures. It is, therefore, an object of at least certain preferred embodiments of the present invention to provide:

New, useful, unique, efficient, non-obvious systems and methods for accurately determining coiled tubing fatigue life and/or deformation;

Such systems and methods which take into account coiled tubing orientation and change thereof during use; and Such systems and method which also provide for controlling such rotation to optimize coiled tubing life and/or minimize deformation.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one skilled in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

DESCRIPTION OF EMBODIMENTS PREFERRED AT THE TIME OF FILING FOR THIS PATENT

Figure 1:
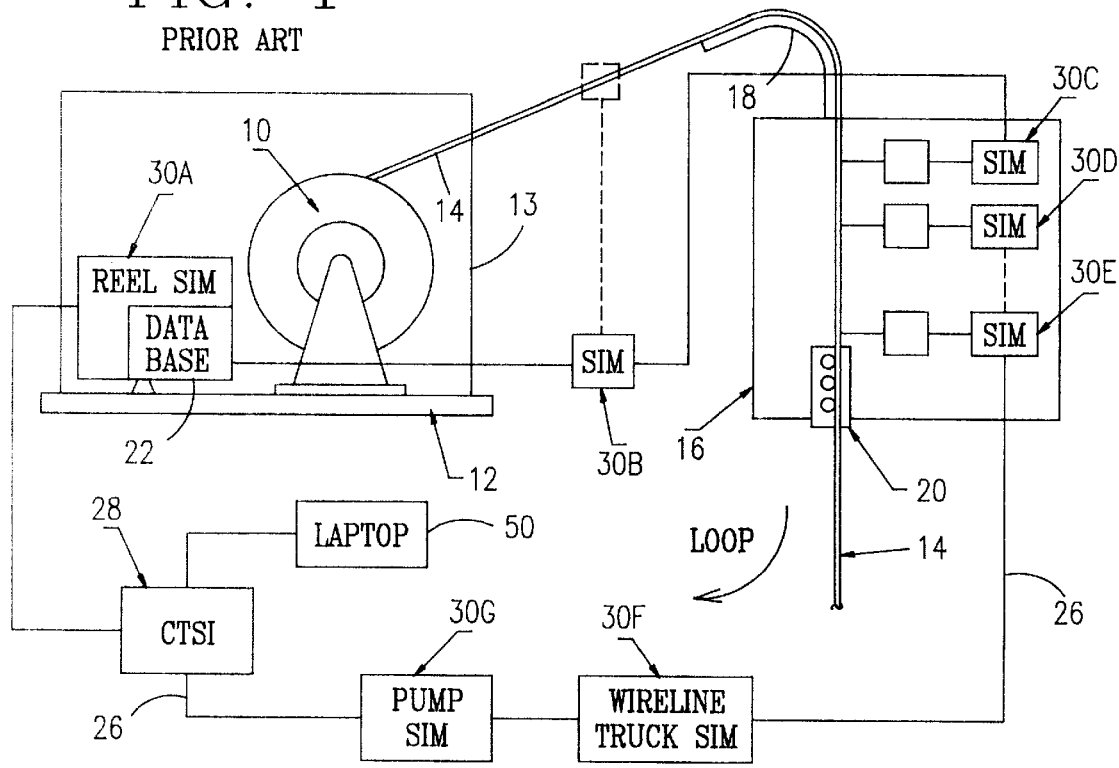
FIG. 1 is a schematic view of a prior art system.
Figure 2:
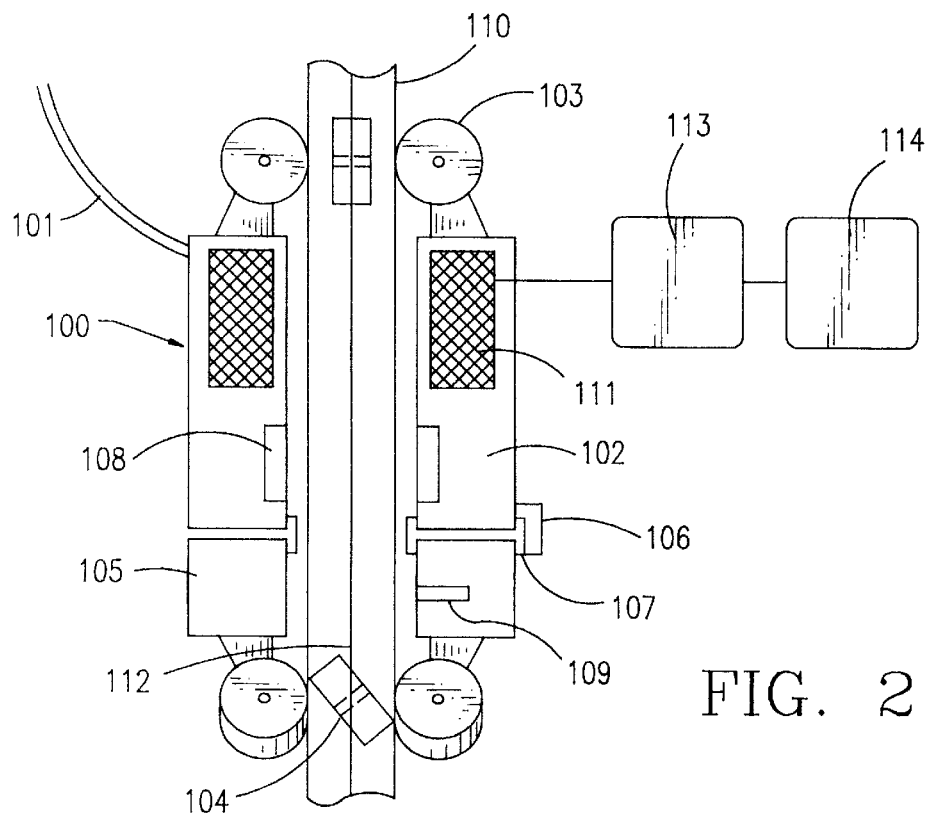
FIG. 2 is a side view of an apparatus useful in methods according to the present invention.

FIG. 2 shows a sensor apparatus 100 for measuring the rotational orientation of coiled tubing using a Hall effect sensor 109 to locate a longitudinal seam weld 112 on coiled tubing 110. Of course, it is within the scope of this invention to employ one or more of any known suitable sensors as discussed above. A support arm 101 attaches the sensor apparatus 100 to a non-moving structure, e.g. but not limited to a guide arch 18 as in FIG. 1. The support arm 101 prevents a non-rotating housing 102 from moving with coiled tubing 110, or rotating about the coiled tubing. A set of wheels 103 attached to the non-rotating housing 102, roll as the coiled tubing 110 moves through the sensor apparatus 100. Another set of wheels 104 are attached to a rotating sensor head 105. These wheels 104 are at an angle to the axis of the coiled tubing 110, causing the rotating sensor head 105 to rotate whenever the coiled tubing 110 moves. A rotational position sensor 106 connected to the non-rotating housing 102 measures the rotational position of the rotating sensor head 105 with respect to the non rotating housing 102. A slip ring and bearing mechanism 107 connected to both the non-rotating housing 102 and the rotating sensor head 150 ties the rotating sensor head 105 to the non-rotating housing 102 both mechanically and electrically. A magnetic coil 108 in the non-rotating housing 102 sets up a magnetic field in the coiled tubing 110. Hall effect sensor(s) 109 in the rotating sensor head 105 measure changes in this magnetic field. A change in this field will occur at the longitudinal seam weld 112. Electronics 111 receive the rotational position from the sensor 106 and Hall effect signals from the sensor(s) 109, and determine the rotational position of the longitudinal seam weld 112, and thus of the coiled tubing 110. This rotational position is transmitted from the electronics 111 to an electronic data acquisition and calculation system, e.g. a computer 113. Optionally the computer 113 is interconnected with a data-transmission/signal-reception system 114 which permits remote control of the system and allows the system to send signals, data, and/or calculations to a remote site.

Figure 3:
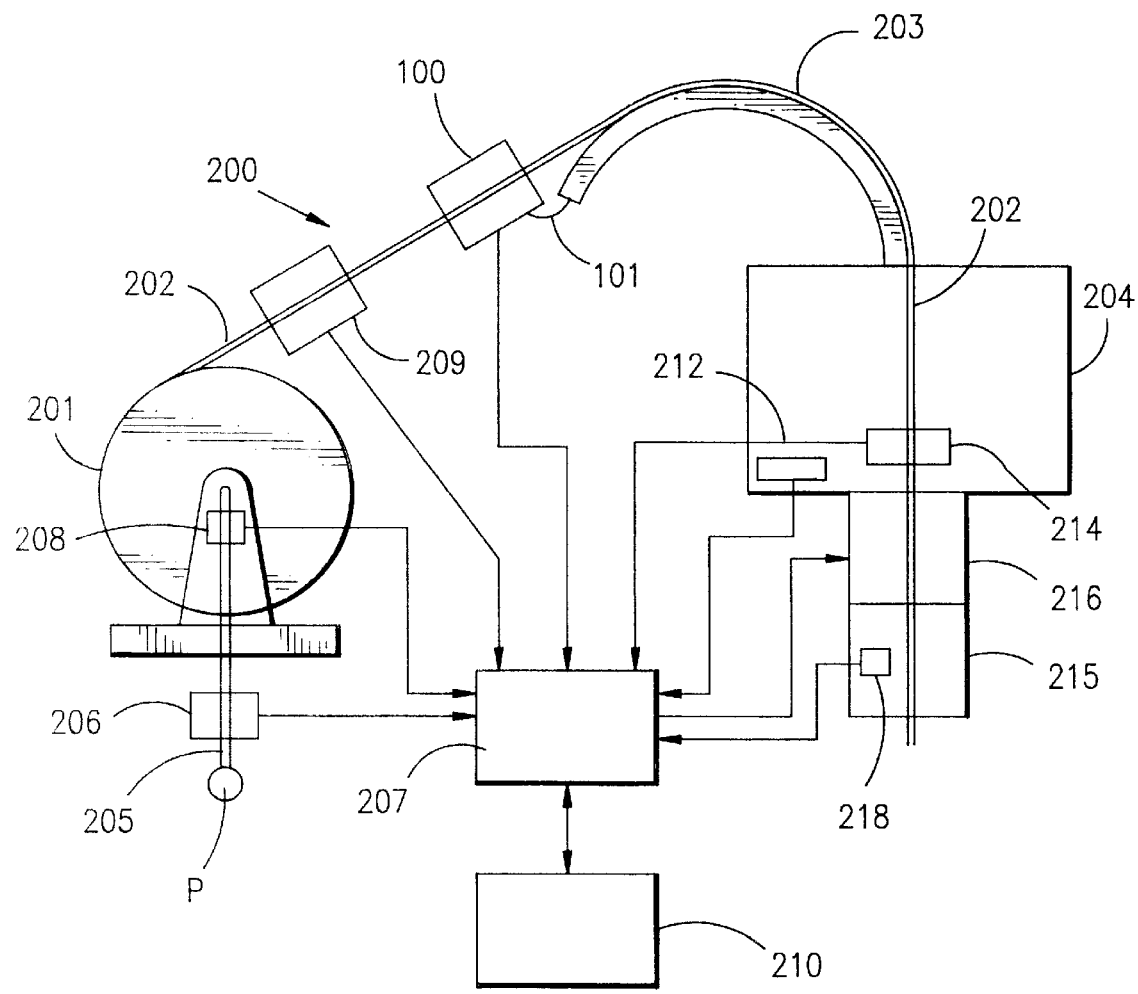
FIG. 3 is a schematic view of a system according to the present invention.

FIG. 3 shows schematically a system 200 according to the present invention which has a typical reel 201 of coil tubing 202 movable over an arch guide 203 and injectable by an injector 204 into a hole or bore. Fluid from a pump P is injected into the coil tubing 202 via high pressure piping 205. A flow meter 206 monitors the flowrate of the fluid and sends a signal indicative thereof to a data acquisition device 207, e.g., but not limited to, an analog to digital signal converter and a microprocessor. The device 207 in turn conveys a signal indicative of fluid flow rate to a computer 210 which may be on site or remote and/or a laptop or base system.

A pressure sensor 208 mounted on the high pressure piping 205 measures the pressure of the fluid from the pump and sends a signal indicative thereof to the data acquisition device 207.

A diameter and ovality gauge 209 mounted to the coiled tubing at the reel measures the coiled tubing's diameter and sends signals indicative thereof to the data acquisition device 207. A sensor 100 (as described above) senses rotation of the coil tubing 202 and sends a signal indicative thereof to the device 207. It is within the scope of the present invention for the gauge 209 and/or the sensor 100 to be appropriately located anywhere in the system and/or to be connected to the reel, arch guide, wellhead, or other structure. The device 207 conveys signals indicative of diameter/ovality and of rotation to the computer 210.

A weight sensor 212 and a depth/speed sensor 214 measure coiled tubing weight and coiled tubing depth and speed, respectively, and transmit signals indicative thereof to the device 207 which, selectively and in turn sends signals corresponding thereto to the computer 210.

Either directly or via the device 207, as shown, the computer 210 selectively sends rotation control signals to a rotation control device 216. The rotation control device may be connected to or adjacent the injector or positioned in any suitable location in the system at which it can effectively control coil tubing rotation.

Typical well control equipment 215 such as a blowout preventer and associated apparatus provides a signal from a pressure sensor 218 to the device 207 indicative of wellhead pressure.

The computer 210 may be one, two or more computers as needed. The device 207 and/or the computer(s) 210 may be located in a central control facility with suitable wiring running therefrom to each device and sensor. In certain aspects, signals coming from the various sensor are analog 4 to 20 ma signals, or digital. pulses. Pressure and weight sensors are typically analog. Depth/speed encoders are a specialized digital pulse. Flowmeters usually output a pulse signal. The data acquisition box 207 converts these electronic signals to "engineering units" such as feet, barrels per minute, etc.—digital data which a computer can read. Communication between the computer 210 and the data acquisition box 207 is via typical standard computer data transmission, e.g. RS 232 serial data transmission. In certain aspects the devices 100 and 200 send a digital data signal which is already readable by a computer, may bypass the device 207 and go directly to the computer 210, which would have required serial com ports. In another aspect these data channels go to the data acquisition device 207 and then through to the computer.

In one method according to the present invention using the computer models, some amount of rotation needed is calculated and this amount is transmitted to the device 207 via a serial cable on which the computer receives data. The device 207 converts this amount to a control signal, typically 0 to 10 V DC, and outputs this signal to the rotation control device 216. The device 207 is programmed with software that among other things handles timing issues, samples each channel in turn, converts signals to engineering units, and checks to insure that pre-set limits are not exceeded (e.g. a high pressure or a CT speed limit).

The present invention, therefore, provides in certain, but not necessarily all embodiments, an assembly including a housing for positioning adjacent movable coiled tubing, and sensing apparatus associated with said housing for sensing rotation of said coiled tubing. Such an assembly with one, some (in any possible combination) and/or all of the following: said sensing apparatus including means for producing and sending an electronic signal indicative of amount of rotation of a portion of said coiled tubing; calculation apparatus interconnected with said sensing apparatus for receiving said electronic signal therefrom and for calculating fatigue life of said portion of said coiled tubing taking said amount of rotation into account; apparatus for continuously recording data concerning rotation of said coiled tubing, said apparatus means for continuously recording data interconnected electronically with said sensing apparatus; parameter sensing apparatus for sensing at least one operating characteristic of said coiled tubing and including characteristic signal apparatus for producing and sending at least one electronic parameter signal indicative of the at least one operating characteristic; wherein the at least one operating characteristic is selected from the group consisting of speed of coiled tubing movement, weight of coiled tubing deployed, depth of coiled tubing deployed, pressure within coiled tubing, internal diameter of coiled tubing, external diameter of coiled tubing, wall thickness of coiled tubing, ovality of coiled tubing and radii of bending of coiled tubing, or is any combination of any of these; calculation apparatus interconnected with said sensing apparatus for receiving said electronic signal therefrom and for calculating fatigue life of said portion of said coiled tubing taking said at least one operating characteristic into account; wherein said at least one operating characteristic is a plurality of operating characteristics; calculation apparatus interconnected with said sensing apparatus for receiving said electronic signal therefrom and for calculating fatigue life of said portion of said coiled tubing taking said amount of rotation into account; wherein said calculation apparatus, optionally, determines optimal rotation orientation of the coiled tubing to minimize the fatigue thereof; an optional rotational control device adjacent the coiled tubing for selectively applying a pre-determined amount of torque thereto to control rotational orientation thereof; wherein the rotational control device moves the coiled tubing to an optimal orientation for reducing fatigue thereof; wherein the at least one operating characteristic is a plurality of operating characteristics, the assembly including apparatus for determining operating characteristics of said coiled tubing including a main data processing unit, cable apparatus extending from said main data processing unit, and sensing apparatus for each of the operating characteristics of said coiled tubing connected to said cable apparatus to provide data to said main data processing unit; apparatus for continuously sensing and recording data concerning said operating characteristics; a reel structure for said coiled tubing on which said coiled tubing is wound and a frame supporting said reel for rotation, said reel structure being transportable; and/or rotation apparatus associated with said housing for rotating said coiled tubing.

The present invention, therefore, provides in certain, but not necessarily all embodiments, an apparatus for determining characteristics of coiled tubing that is run in and out of a bore for calculating fatigue life of the coiled tubing, said apparatus including a reel structure for said coiled tubing including a reel on which said coiled tubing is wound and a frame supporting the reel for rotation, an injector structure for running the coiled tubing from the reel structure into said bore and for withdrawing said coiled tubing from the bore, sensor apparatus for continuously monitoring sensing and recording rotation of said coiled tubing and for measuring amount of said rotation, said sensor apparatus including apparatus for receiving and transmitting data relating to said characteristics of the coiled tubing, and a computer apparatus (one or more computers) for receiving data from said sensor apparatus and processing said data to determine fatigue life of said coiled tubing; such apparatus with parameter sensing apparatus for sensing at least one operating characteristic of said coiled tubing and including characteristic signal apparatus for producing and sending at least one electronic parameter signal indicative of the at least one operating characteristic, wherein the at least one operating characteristic is selected from the group consisting of speed of coiled tubing movement, weight of coiled tubing deployed, length of coiled tubing deployed pressure within coiled tubing, internal diameter of coiled tubing, external diameter of coiled tubing, wall thickness of coiled tubing, and radii of bending of coiled tubing, and wherein said computer means receives said electronic parameter signal and utilizes said at least one operating characteristic in determining fatigue life of the coiled tubing; and/or a rotational control device positioned adjacent the coiled tubing for selectively applying torque thereto to control rotational orientation thereof.

The present invention, therefore, provides in certain, but not necessarily all embodiments, a method for measuring rotation of coiled tubing, said method including moving coiled tubing through an assembly into a bore, said assembly like any disclosed herein, and determining amount of rotation of the coiled tubing with said sensing apparatus; and such a method wherein said assembly includes rotation apparatus associated with said housing for rotating said coiled tubing and said method includes rotating said coiled tubing with said rotation apparatus.

The present invention, therefore, provides in certain, but not necessarily all embodiments, a method for determining fatigue life of coiled tubing, the method including moving coiled tubing into a bore through an apparatus, the apparatus including a reel structure, an injector structure, and sensor apparatus as disclosed herein; sensing rotation of a portion of the coiled tubing with the sensor apparatus and transmitting data related thereto to computer apparatus; and determining with the computer apparatus the fatigue life of said portion of said coiled tubing.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112. The inventors may rely on the Doctrine of Equivalents to determine and assess the scope of their invention and of the claims that follow as they may pertain to apparatus not materially departing from, but outside of, the literal scope of the invention as set forth in the following claims.

What is claimed is:

1. Apparatus for calculating fatigue life of coiled tubing that is run in and out of a bore, said apparatus comprising
   a reel structure for said coiled tubing including a reel on which said coiled tubing is wound and a frame supporting the reel for rotation,
   an injector structure for running the coiled tubing from the reel structure into said bore and for withdrawing said coiled tubing from the bore,
   sensor means for continuously monitoring sensing and recording rotation of said coiled tubing and for measuring amount of said rotation, said sensor means including means for receiving and transmitting data relating to said rotation of said coiled tubing and to said amount of said rotation, and
   a computer means for receiving data from said sensor means and processing said data to determine fatigue life of said coiled tubing.

2. The apparatus of claim 1 further comprising
   parameter sensing apparatus for sensing at least one operating characteristic of said coiled tubing and including characteristic signal means for producing and sending at least one electronic parameter signal indicative of the at least one operating characteristic,
   wherein the at least one operating characteristic is selected from the group consisting of speed of coiled tubing movement, weight of coiled tubing deployed, length of coiled tubing deployed pressure within coiled tubing, internal diameter of coiled tubing, external diameter of coiled tubing, wall thickness of coiled tubing, and radii of bending of coiled tubing, and wherein said computer means receives said electronic parameter signal and utilizes said at least one operating characteristic in determining fatigue life of the coiled tubing.

3. The method of claim 2 wherein said assembly includes rotation apparatus associated with said housing for rotating said coiled tubing and said method further comprising
   rotating said coiled tubing with said rotation apparatus.

4. The assembly of claim 1 further comprising
   a rotational control device positioned adjacent the coiled tubing for selectively applying torque thereto to control rotational orientation thereof.

5. A method for determining fatigue life of coiled tubing, the method comprising the steps of
   moving coiled tubing into a bore through an apparatus, the apparatus comprising a reel structure for said coiled tubing including a reel on which said coiled tubing is wound and a frame supporting the reel for rotation, an injector structure for running the coiled tubing from the reel structure into said bore and for withdrawing said coiled tubing from the bore, sensor means for continuously monitoring sensing and recording rotation of said coiled tubing and for measuring amount of said rotation, said sensor means including means for receiving and transmitting data relating to said characteristics of the coiled tubing, and a computer means for receiving data from said sensor means and processing said data to determine fatigue life of said coiled tubing,
   sensing with the sensor means rotation of a portion of the coiled tubing previously moved into the bore by the apparatus, and transmitting data related thereto to the computer means, and
   determining with the computer means the fatigue life of said portion of said coiled tubing.

* * * * *